United States Patent
Ma et al.

(10) Patent No.: US 9,023,357 B2
(45) Date of Patent: *May 5, 2015

(54) ANTI-PROLACTIN RECEPTOR ANTIBODY FORMULATIONS

(71) Applicant: Bayer HealthCare LLC, Whippany, NJ (US)

(72) Inventors: Xinghang Ma, Dublin, CA (US); Jianjie Niu, Castro Valley, CA (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/213,497

(22) Filed: Mar. 14, 2014

(65) Prior Publication Data

US 2014/0271659 A1 Sep. 18, 2014

Related U.S. Application Data

(60) Provisional application No. 61/799,629, filed on Mar. 15, 2013.

(51) Int. Cl.
*A61K 39/395* (2006.01)
*C07K 16/28* (2006.01)

(52) U.S. Cl.
CPC ....... *C07K 16/2869* (2013.01); *A61K 39/39591* (2013.01); *C07K 2317/21* (2013.01); *C07K 2317/52* (2013.01); *C07K 2317/76* (2013.01); *C07K 2317/94* (2013.01)

(58) Field of Classification Search
CPC ............... C07K 16/28; C07K 16/2869; C07K 2317/21; C07K 2317/76; C07K 2317/94; A61K 39/395; A61K 39/3955; A61K 39/39591

See application file for complete search history.

(56) References Cited

U.S. PATENT DOCUMENTS

| | | | |
|---|---|---|---|
| 7,867,493 B2 * | 1/2011 | Damiano et al. | 424/133.1 |
| 2011/0158987 A1 | 6/2011 | Adler et al. | |
| 2014/0065158 A1 * | 3/2014 | Ma et al. | 424/142.1 |

FOREIGN PATENT DOCUMENTS

| | | |
|---|---|---|
| EP | 2332995 A1 | 6/2011 |
| WO | WO 2004055164 A2 * | 7/2004 |
| WO | WO 2006044908 A2 * | 4/2006 |
| WO | 2008084106 A1 | 7/2008 |
| WO | 2010031720 A2 | 3/2010 |
| WO | 2010066762 A1 | 6/2010 |
| WO | 2010129469 A1 | 11/2010 |
| WO | 2014036076 A1 | 3/2014 |

OTHER PUBLICATIONS

Paul et al., "Long-term stability of bevacizumab repackaged in 1 mL polypropylene syringes for intravitreal administration", Annales Pharmaceutiques Francaises; 2012; 16 pages.
International Search Report and Written Opinion for PCT/US2014/028078 dated Jul. 16, 2014; 16 pages.

* cited by examiner

*Primary Examiner* — Ruixiang Li
(74) *Attorney, Agent, or Firm* — Armstrong Teasdale LLP

(57) ABSTRACT

Provided are a wide concentration range, especially high concentration anti-prolactin receptor antibody formulations that are substantially isosmotic and of low viscosity.

18 Claims, No Drawings

ANTI-PROLACTIN RECEPTOR ANTIBODY FORMULATIONS

CROSS-REFERENCE TO RELATED APPLICATIONS

The present application is a continuation application of U.S. Application No. 61/799,629, entitled "ANTI-PROLACTIN RECEPTOR ANTIBODY FORMULATIONS" and filed Mar. 15, 2013, the entire disclosure of which is expressly incorporated herein by reference.

SEQUENCE LISTING SUBMISSION

The present application includes a Sequence Listing in electronic format as a txt file titled "Sequence_Listing_17207-0007USU1_ST25," which was created on Mar. 13, 2014 and which has a size of 14.8 kilobytes (KB). The contents of txt file "Sequence_Listing_17207-0007USU1_ST25" are incorporated by reference herein.

BACKGROUND

The present disclosure relates generally to a wide concentration range of anti-prolactin receptor antibody formulations that are substantially isosmotic and of low viscosity, including formulations that are useful for subcutaneous and general injection administration.

Prolactin (PRL) is a polypeptide hormone composed of 199 amino acids. PRL belongs to the growth hormone (GH), placental lactogen (PL) family of polypeptide hormones and is synthesized in lactotroph cells of the pituitary and in several extrapituitary tissues such as lymphocytes, mammary epithelial cells, the myometrium, and the prostate. Two different promoters regulate pituitary and extrapituitary PRL synthesis (*BioEssays* 28:1051-1055 (2006)).

PRL binds to the PRL receptor (PRLR), a single transmembrane receptor belonging to the class 1 cytokine receptor superfamily (*Endocrine Reviews* 19:225-268 (1998)). PRLR exists in three different isoforms, the short, the long, and the intermediate form that can be distinguished by the length of their cytoplasmic tails. Upon ligand binding, a sequential process leads to PRLR activation. PRL interacts via its binding site 1 with one PRLR molecule and then attracts via its binding site 2 a second receptor molecule leading to an active dimer of PRLRs.

PRLR dimerization leads to the predominant activation of the JAK/STAT (Janus Kinase/Signal transducers and activators of transcription) pathway. Upon receptor dimerization, JAKs (predominantly JAK2) associated with the receptor, transphosphorylate and activate each other. In addition the PRLR is also phosphorylated and can bind to SH2-domain containing proteins such as STATs. Receptor bound STATs are subsequently phosphorylated, dissociate from the receptor and translocate to the nucleus where they stimulate transcription of target genes. In addition, activation of the Ras-Raf-MAPK pathway and activation of the cytoplasmic src kinase by PRLRs have been described (for review *Endocrine Reviews* 19: 225-268 (1998)).

The role of PRLR-mediated signalling has been investigated in the context of the benign disease endometriosis. In one study the expression pattern of the PRLR in endometriotic samples and eutopic endometrium from endometriosis patients was analysed (*Acta Obstet Gynecol Scand* 81:5-10, 2002) during the mid-late proliferative phase of the menstrual cycle. It was demonstrated that the PRLR mRNA was present in the eutopic endometrium in 79% of the analysed endometriosis patients, whereas it was absent in the endometriotic lesions in 86% of the endometriosis patients. These data suggested a possible differential regulation of PRLR expression between normal and endometriotic tissue. However, from these expression data it cannot be concluded that inhibition of the PRLR might represent a suitable endometriosis therapy—especially since the PRLR was not found to be expressed in the endometriotic lesions (*Acta Obstet Gynecol Scand* 81:5-10 (2002)).

Antibodies that are directed against prolactin receptor (PRLR), including anti-PRLR monoclonal antibodies (aPRLR mAbs), are being developed in an effort to block PRLR function. One such aPRLR mAb is an IgG2 anti-PRLR mAb that is being developed for the non-hormonal treatment of endometriosis patients.

Antibodies may be administered to patients via intravenous, intramuscular, and/or subcutaneous injection. To ensure patient compliance, it is desirable that intramuscular and subcutaneous injection dosage forms be isotonic and include small injection volumes (<2 ml per injection site). To reduce injection volume, and to provide an effective dose, antibodies are often administered with a wide concentration range, from 0.1-150 mg/mL, including high concentrations within the range of 20 mg/ml to 150 mg/ml.

While both liquid and lyophilized dosage forms are used for currently marketed antibody drug products, lyophilized forms are more frequently used for antibody drug products having high protein concentrations. A high concentration antibody dosage form may present many challenges in formulation development, especially for liquid formulation. For formulations in which the antibody concentration is near its apparent solubility limit, phase separation can occur through precipitation, gelation, and/or crystallization. At high protein concentration, the stability of an antibody can become problematic due to the formation of soluble and insoluble protein-protein aggregates. Highly concentrated antibody formulations are frequently highly viscous, which presents difficulties for processing, such as ultrafiltration and sterile filtration, and for injection of the dosage solution. And at high antibody concentrations, which are desirable for formulations intended for intramuscular or subcutaneous administration, proportionally high concentrations of stabilizers, such as sucrose and sodium chloride, are required to achieve long-term protein stability. The resulting hypertonic solutions often cause injection pain due to tissue damage. Therefore, it is often desirable to balance the amount of stabilizers for stability and osmolality of the high protein concentration formulation.

SUMMARY

The present disclosure provides liquid and lyophilized anti-PRLR antibody formulations with a wide range of anti-PRLR antibody concentrations, which are substantially isotonic and low viscosity. The anti-PRLR antibody formulations contain substantially no salt other than an organic salt or an inorganic salt, such as a phosphate salt, that is used to buffer the formulation.

The anti-PRLR antibody formulations presented herein contain from about 0 mM to about 30 mM phosphate such as, for example, sodium phosphate and/or potassium phosphate; from about 50 ppm to about 200 ppm of a non-ionic surfactant such as, for example, polysorbate (Tween®) 80 and/or polysorbate (Tween®) 20; from about 88 mM to about 292 mM of a sugar or sugar alcohol such as, for example, mannitol, dextrose, glucose, trehalose, and/or sucrose; from about 0 mM to about 50 mM arginine; from about 0 mM to about 50 mM lysine; from about 0 mM to about 270 mM glycine or alanine; from about 0 mM to about 10 mM methionine; and from about 0.1 mg/ml to about 150 mg/ml of an anti-PRLR antibody, including an aPRLR-specific IgG2 monoclonal antibody (mAb) at a pH from about pH 5.5 to about pH 6.5.

Each of the presently disclosed antibody formulations contains substantially no salt other than an organic salt or an inorganic salt, such as a phosphate salt, that is used to buffer the formulation, which permits the addition of alternative stabilizers to maintain the isosmoticity of the formulation (i.e., osmolality ranging from about 240 mmol/kg to about 380 mmol/kg), which thereby promotes a higher degree of patient compliance.

Each of the presently disclosed antibody formulations has a low viscosity ranging from about 1 to about 8 mPa-S at 22° C.-23° C., which promotes ease of processing such as, for example, improved ultrafiltration and sterile filtration as well as injection of the antibody formulation through a syringe needle during administration.

The formulations disclosed herein stabilize antibodies, in particular anti-PRLR antibodies including anti-PRLR IgG2 antibodies, at high protein concentrations in liquid form or in lyophilized form.

DESCRIPTION OF VARIOUS EMBODIMENTS

As described above, the present disclosure provides anti-PRLR antibody formulations that stabilize the anti-PRLR antibody in a wide range of concentration in liquid form or in lyophilized form at intended storage conditions. The formulations described herein include one or more pharmaceutically acceptable excipients or stabilizers, and are contained in buffered media at a suitable pH and are substantially isosmotic with physiological fluids. For systemic administration, injection is one possible route of administration, including intramuscular, intravenous, intraperitoneal, and subcutaneous for injection.

Because of their low viscosity, the presently disclosed anti-PRLR antibody formulations can be conveniently processed via, for example, ultrafiltration and sterile filtration and can be administered to a patient via injection, including both intravenous and subcutaneous injection. Moreover, because they are substantially isosmotic, the presently disclosed anti-PRLR antibody formulations reduce tissue damage or other adverse physiologic effects and thereby achieving favorable patient tolerance and increased patient compliance.

The formulations described herein are characterized by the substantial absence of added salt other than an organic salt or an inorganic salt, such as a phosphate salt, that is used to buffer the formulation, which provides the flexibility for increasing the concentrations of other stabilizers, such as sucrose, while maintaining the osmolality of the formulation for improved in vivo tolerability and, consequently, increased patient compliance. Moreover, the low viscosity of the presently described formulations permits convenient processing, including ultrafiltration and sterile filtration, and injection of the drug product solution through the needle.

For the purpose of interpreting this specification, the following definitions will apply. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

Whenever appropriate, terms used in the singular also will include the plural and vice versa. The use of "a" herein means "one or more" unless stated otherwise or where the use of "one or more" is clearly inappropriate. The use of "or" means "and/or" unless stated otherwise. The use of "comprise," "comprises," "comprising," "include," "includes," and "including" are interchangeable and not intended to be limiting. The term "such as," "for example," and "e.g." also are not intended to be limiting. For example, the term "including" shall mean "including, but not limited to." Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "viscosity" refers to the resistance of a liquid formulation to flow, such as when injected through a syringe needle during administration to a patient. Viscosity measurements can be done by a cone and plate technique with a Peltier element set at a defined temperature, such as 22° C. as described herein. Typically, a well-defined shear stress gradient is applied to the liquid formulation and the resulting shear rate is measured. The viscosity is the ratio of the shear stress to the shear rate. As used herein, viscosity is expressed in units of mPa-S at 22° C. wherein 1 mPa-S=1 cP. The high concentration, low viscosity, substantially isosmotic formulations disclosed herein are typically characterized by having a viscosity ranging from 1 to 8 mPa-S at 22° C.-23° C.

As used herein, the term "osmolality" refers to a measure of solute concentration, defined as the number of mmole of solute per kg of solution. A desired level of osmolality can be achieved by the addition of one or more stabilizer such as a sugar or a sugar alcohol including mannitol, dextrose, glucose, trehalose, and/or sucrose. Additional stabilizers that are suitable for providing osmolality are described in references such as the handbook of Pharmaceutical Excipients (Fourth Edition, Royal Pharmaceutical Society of Great Britain, Science & Practice Publishers) or Remingtons: The Science and Practice of Pharmacy (Nineteenth Edition, Mack Publishing Company).

As used herein, the term "about" refers to +/−10% of the unit value provided. As used herein, the term "substantially" refers to the qualitative condition of exhibiting a total or approximate degree of a characteristic or property of interest. One of ordinary skill in the biological arts will understand that biological and chemical phenomena rarely, if ever, achieve or avoid an absolute result because of the many variables that affect testing, production, and storage of biological and chemical compositions and materials, and because of the inherent error in the instruments and equipment used in the testing, production, and storage of biological and chemical compositions and materials. The term substantially is therefore used herein to capture the potential lack of completeness inherent in many biological and chemical phenomena.

As used herein, the terms "isosmotic" and "isotonic" are used interchangeably with the terms "substantially isosmotic," and "substantially isotonic" and refer to formulations characterized by having an osmotic pressure that is the same as or at least substantially equivalent to the osmotic pressure of another solution, which is achieved by formulations wherein the total concentration of solutes, including both permeable and impermeable solutes, in the formulation are the same as or at least substantially equivalent to the total number of solutes in another solution. Thus, while it will be appreciated by those of skill in the art that "isosmotic" and "isotonic" formulations that are used for in vivo administration generally have an osmolality ranging from about 270 mmol/kg to about 310 mmol/kg, in the context of the high concentration, low viscosity formulations of the present disclosure, the terms "isosmotic," "isotonic," "substantially isosmotic," and "substantially isotonic" are used interchangeably to refer to formulations having an osmolality ranging from about 240 mmol/kg to about 380 mmol/kg, or from about 270 mmol/kg to about 370 mmol/kg, or from about 300 mmol/kg to about 330 mmol/kg.

The presently disclosed high concentration, low viscosity, substantially isosmotic anti-PRLR antibody formulations contain from about 0 mM to about 30 mM phosphate such as, for example, sodium phosphate and/or potassium phosphate; from about 50 ppm to about 200 ppm of a non-ionic surfactant such as, for example, polysorbate (Tween®) 80 and/or polysorbate (Tween®) 20; from about 34 mM to about 292 mM of a sugar or sugar alcohol, such as, for example, mannitol, dextrose, glucose, trehalose, and/or sucrose; from about 0 mM to about 50 mM arginine; from about 0 mM to about 50 mM lysine; from about 0 mM to about 270 mM glycine or alanine; from about 0 mM to about 10 mM methionine; and from about 2 mg/ml to about 150 mg/ml of an anti-PRLR antibody at a pH from about pH 5.5 to about pH 6.5. The formulations disclosed herein exhibit a viscosity ranging from about 1 to about 8 mPa-S at 22° C.-23° C. and osmolality ranging from about 240 to about 380 mmol/kg.

In these formulations, phosphate is a buffer agent, which can be used to maintain the formulation pH from about pH 5.5 to about pH 6.5, or from about pH 5 to about pH 6, such as about pH 5.5, about pH 5, about pH 5.5, about pH 6, or about pH 6.5.

Sugars or sugar alcohol, such as mannitol, dextrose, glucose, trehalose, and/or sucrose, are used separately or in combination both as cryo-protectants and a stabilizer the anti-PRLR antibody in liquid formulations as well as during lyophilization.

Non-ionic surfactants such as polysorbates, including polysorbate 20 and polysorbate 80; polyoxamers, including poloxamer 184 and 188; Pluronic® polyols; and other ethylene/polypropylene block polymers, stabilize the anti-PRLR antibody during processing and storage by reducing interfacial interaction and prevent antibody from adsorption.

Arginine is a protein solubilizer and also a stabilizer that reduces antibody and other protein aggregation, such as anti-PRLR antibody aggregation, and other possible degradation. Methionine is an antioxidant that prevents antibody oxidation during processing and storage.

Sugars and inorganic salts are commonly used as protein stabilizers; however, both sugars and inorganic salts are also effective tonicity agents. If a formulation requires a high concentration of one or more sugars to stabilize an anti-PRLR antibody, the inorganic salt concentration should be zero or kept very low in order to maintain the formulation's osmolality such that injection pain is reduced upon administration.

As used herein, the term "salt" refers to inorganic salts, which include sodium chloride (NaCl), sodium sulfate ($Na_2SO_4$), sodium thiocyanate (NaSCN), magnesium chloride (MgCl), magnesium sulfate ($MgSO_4$), ammonium thiocyanate ($NH_4SCN$), ammonium sulfate (($NH_4)_2SO_4$), ammonium chloride ($NH_4Cl$), calcium chloride ($CaCl_2$), calcium sulfate ($CaSO_4$), zinc chloride ($ZnCl_2$) and the like, or combinations thereof. The anti-PRLR antibody formulations disclosed herein are characterized by a substantial absence of added salt and are, therefore, referred to herein as salt-free antibody formulations. It will be understood by those of skill in the art that the presence of inorganic salts within the presently disclosed formulations that are introduced by pH adjustment are not considered to be added salts. Such inorganic salts when introduced by pH adjustments, if present in a formulation according to the present disclosure, should not exceed a concentration of about 5 mM.

As used herein, the term "surfactant" includes non-ionic surfactants including, without limitation, polysorbates, such as polysorbate 20 or 80, and the polyoxamers, such as poloxamer 184 or 188, Pluronic® polyols, and other ethylene/polypropylene block polymers. Amounts of surfactants effective to provide stable high concentration anti-PRLR antibody formulations are usually in the range of 50 ppm to 200 ppm. The use of non-ionic surfactants permits the formulations to be exposed to shear and surface stresses without causing denaturation of the anti-PRLR antibody, and also reduce the adsorption on the surfaces during processing and storage. The formulations disclosed herein include, without limitation, formulations having one or more non-ionic surfactant(s) including, for example, one or more polysorbate(s), such as polysorbate 20 or 80; one or more polyoxamers, such as poloxamer 184 or 188; Pluronic® polyols; and/or one or more ethylene/polypropylene block polymer(s). Exemplified herein are formulations having a polysorbate, such as polysorbate 20 (Tween® 20) or polysorbate 80 (Tween® 80).

As used herein, the term "antibody" refers to a class of proteins that are generally known as immunoglobulins. Antibodies include full-length monoclonal antibodies (mAb), such as IgG2 monoclonal antibodies, which include immunoglobulin Fc regions. The term antibody also includes bispecific antibodies, diabodies, single-chain molecules, and antibody fragments such as Fab, $F(ab')_2$, and Fv.

As used herein, the term "anti-PRLR antibody" refers to an antibody having binding specificity against the human PRLR protein as well as fragments and variants of the human PRLR protein. Anti-PRLR antibodies presented herein can be IgG2 antibodies and include anti-PRLR IgG2 monoclonal antibodies, such as chimeric, humanized, and fully-human anti-PRLR IgG2 monoclonal antibodies. Anti-PRLR monoclonal antibodies, including full-length antibodies and antigen binding fragments and variants thereof, that are suitable for use in the formulations disclosed herein are presented in PCT Patent Publication NOs. WO/2011/069799, WO/2011/069798, WO/2011/069797, WO/2011/069796, WO/2011/069795, and WO/2011/069794, each of which are incorporated by reference herein in their entirety.

"Monoclonal antibodies" are characterized by having specificity for a single antigenic determinant. Monoclonal antibodies can, for example, be made by the hybridoma method described by Kohler and Milstein, *Nature* 256:495 (1975) or by recombinant DNA methods such as those described in U.S. Pat. No. 4,816,567. Monoclonal antibodies can also be isolated from phage display libraries using the techniques such as those described in Clackson et al., *Nature* 352:624-628 (1991) and Marks et al., *J. Mol. Biol.* 222:581-597 (1991).

Monoclonal antibodies include "chimeric monoclonal antibodies" wherein a portion of a heavy and/or light chain includes sequences from antibodies derived from one species, while the remainder of the antibody, including the Fc region, includes sequences from antibodies derived from a second species, and the second species may be human. See, e.g., U.S. Pat. No. 4,816,567 and Morrison et al., *Proc. Natl. Acad. Sci. USA* 81:6851-6855 (1984).

Monoclonal antibodies also include "humanized monoclonal antibodies" wherein one or more complementarity determining region (CDR) from a heavy and/or light chain sequence from antibodies derived from one species replace one or more CDR from a heavy and/or light chain sequence from antibodies derived from a second species, and the second species may be human. The process of "humanization" is usually applied to monoclonal antibodies developed for administration to humans. See, e.g., Riechmann et al., *Nature* 332(6162):323-27 (1988) and Queen et al., *Proc. Natl. Acad. Sci. USA* 86(24):10029-33 (1989).

Monoclonal antibodies also include "fully-human monoclonal antibodies" wherein the entire heavy and light chain sequences are derived from human antibody sequences. Fully-human monoclonal antibodies can be generated by phage display technologies and can be isolated from mice that have been genetically engineered to express the human antibody repertoire. See, e.g., McCafferty et al., *Nature* 348(6301):552-554 (1990), Marks et al., *J. Mol. Biol.* 222(3): 581-597 (1991), and Carmen and Jermutus, *Brief Funct. Genomic Proteomic* 1(2):189-203 (2002).

As used herein, the term "Pharmaceutically effective amount" of an anti-PRLR antibody formulation refers to an amount of the formulation that provides therapeutic effect in an administration regimen. The high concentration anti-PRLR antibody formulations disclosed herein typically include an anti-PRLR antibody at a concentration ranging from about 1 mg/ml to about 150 mg/ml, or from about 2 mg/ml to about 120 mg/ml, or from about 5 mg/ml to about 100 mg/ml, or from about 7.5 mg/ml to about 60 mg/ml. Within some aspects the concentration of anti-PRLR antibody within these formulations is about 7.5 mg/ml, or about 20 mg/ml, or about 60 mg/ml. Such formulations are typically administered in a volume of less than about 2 ml, or about 1.5 ml, or about 1 ml, or about 0.5 ml per injection site.

Within other aspects, the anti-PRLR antibody formulation contains about 10 mM sodium phosphate, about 263 mM sucrose, about 80 ppm polysorbate 80, about 20 mM arginine, about 60 mg/mL anti-PRLR antibody at a pH ranging from about pH 5.5 to about pH 6.5, such as pH 6.5.

Within other aspects, the anti-PRLR antibody formulation contains about 10 mM sodium phosphate, about 263 mM sucrose, about 80 ppm polysorbate 80, about 20 mM arginine, about 60 mg/mL anti-PRLR antibody at a pH ranging from about pH 0.5 to about pH 6.5, such as pH 6.0.

Within other aspects, the anti-PRLR antibody formulation contains about 10 mM sodium phosphate, about 263 mM sucrose, about 80 ppm polysorbate 80, about 60 mg/mL anti-PRLR antibody at a pH ranging from about pH 5 to about pH 6.5, such as pH 5.5.

Within other aspects, the anti-PRLR antibody formulation contains about 10 mM sodium phosphate, about 263 mM sucrose, about 80 ppm polysorbate 80, about 10 mM arginine, about 1 mM methionine, about 60 mg/mL anti-PRLR antibody at a pH ranging from about pH 5.5 to about pH 6.5, such as pH 6.0.

Within other aspects, the anti-PRLR antibody formulation contains about 10 mM sodium phosphate, about 263 mM sucrose, about 80 ppm polysorbate 80, about 10 mM arginine, about 1 mM methionine, about 60 mg/mL anti-PRLR antibody at a pH ranging from about pH 5.5 to about pH 6.5, such as pH 6.5.

Thus, the present disclosure provides anti-PRLR mAb formulations, including anti-PRLR IgG2 mAb formulations, wherein the anti-PRLR mAb is soluble at high protein concentrations. Typically, the anti-PRLR mAb in the formulations disclosed herein remain soluble at concentrations of between about 1 mg/ml to about 150 mg/ml and remain stable under isosmotic storage conditions and exhibit reduced viscosity as compared to currently available antibody formulations.

The anti-PRLR antibody having a light chain comprising the amino acid sequence of SEQ ID NO: 1 and a heavy chain comprising the amino acid sequence of SEQ ID NO: 7 is an IgG2 antibody that blocks prolactin receptor (PRLR). Anti-PRLR antibodies can prevent the onset or progression of endometriosis by blocking PRLR, thereby overcoming deficiencies in endometrial pathways. The high concentration, salt free anti-PRLR antibody formulations presented herein can be administrated to the patients via intravenous injection or subcutaneous injection or other injection routes.

As part of the present disclosure, stability of anti-PRLR antibodies is affected by excipients. The stability of anti-PRLR antibody increases with the decrease of NaCl concentrations. In addition, positively charged amino acids, such as arginine and lysine, can improve the stability anti-PRLR antibody and that pH greatly affects anti-PRLR antibody aggregation. The aggregation of antibody solutions increases with increases in pH. The optimal pH for stabilizing the anti-PRLR antibodies presented herein ranges from about pH 5.5 to about pH 6.5 about pH 6, or about pH 6.5.

Provided herein are anti-PRLR antibody formulations wherein the anti-PRLR antibodies include IgG2 antibodies, including human IgG2 monoclonal anti-PRLR antibodies having a light chain sequence and a heavy chain sequence presented in one or more of PCT Patent Publication NOs. WO/2011/069799, WO/2011/069798, WO/2011/069797, WO/2011/069796, WO/2011/069795, and WO/2011/069794.

Antibodies that may be suitably employed in the anti-PRLR antibody formulations described herein are exemplified by the Mat3-hIgG2 antibody presented in Table 1, which was obtained from the BioInvent Phage Display library (Lund, Sweden) and subsequently germlined and sequence-optimized for affinity, activity, species cross-reactivity, and manufacturability.

The Fab part comprises a lambda light chain (VL: DPL3 germline; CL: Mcg-/Kern-/Oz-isotype) and a heavy chain VH DP47-germline framework region. The antibody was reformatted into a human IgG2 of the IgG2m (n-) heavychain allotype lacking the C-terminal lysine. A potential deamidation site is present in CDR3 at amino acid position 98 of the light chain and was left unchanged in this antibody. The standard N-glycosylation site of IgG2 is present at N294 of the heavy chain.

TABLE 1

Heavy and Light Chain Sequences of Exemplary Human Anti-PRLR IgG2 Monoclonal Antibody Mat3-hIgG2

| Sequence Identifier | Portion of Antibody Chain | Amino Acid Sequence ($NH_3$—COOH) |
|---|---|---|
| SEQ ID NO: 1 | Light Chain, Full-length | QSVLTQPPSA SGTPGQRVTI SCTGSSSNIG AGYVVHWYQQ LPGTAPKLLI YRNNQRPSGV PDRFSGSKSG TSASLAISGL RSEDEADYYC AAWDDSLNGW |

TABLE 1-continued

Heavy and Light Chain Sequences of Exemplary Human Anti-PRLR IgG2 Monoclonal Antibody Mat3-hIgG2

| Sequence Identifier | Portion of Antibody Chain | Amino Acid Sequence (NH3—COOH) |
|---|---|---|
| | | LFGGGTKLTV LGQPKAAPSV<br>TLFPPSSEEL QANKATLVCL<br>ISDFYPGAVT VAWKADSSPV<br>KAGVETTTPS KQSNNKYAAS<br>SYLSLTPEQW KSHRSYSCQV<br>THEGSTVEKT VAPTECS |
| SEQ ID NO: 2 | Light Chain, Variable Domain | QSVLTQPPSA SGTPGQRVTI<br>SCTGSSSNIG AGYVVHWYQQ<br>LPGTAPKLLI YRNNQRPSGV<br>PDRFSGSKSG TSASLAISGL<br>RSEDEADYYC AAWDDSLNGW<br>LFGGGTKLTV LGQ |
| SEQ ID NO: 3 | Light Chain, Variable Domain, CDR1 | SCTGSSSNIG AGYVVH |
| SEQ ID NO: 4 | Light Chain, Variable Domain, CDR2 | RNNQRPS |
| SEQ ID NO: 5 | Light Chain, Variable Domain, CDR3 | CAAWDDSLNG WL |
| SEQ ID NO: 6 | Light Chain, Constant Domain | PKAAPSVTLF PPSSEELQAN<br>KATLVCLISD FYPGAVTVAW<br>KADSSPVKAG VETTTPSKQS<br>NNKYAASSYL SLTPEQWKSH<br>RSYSCQVTHE GSTVEKTVAP<br>TECS |
| SEQ ID NO: 7 | Heavy Chain, Full-length | EVQLLESGGG LVQPGGSLRL<br>SCAASGFTFS SYWMHWVRQA<br>PGKGLEWVSD IARLSSYTNY<br>ADSVKGRFTI SRDNSKNTLY<br>LQMNSLRAED TAVYYCARGL<br>DARRMDYWGQ GTLVTVSSAS<br>TKGPSVFPLA PCSRSTSEST<br>AALGCLVKDY FPEPVTVSWN<br>SGALTSGVHT FPAVLQSSGL<br>YSLSSVVTVP SSNFGTQTYT<br>CNVDHKPSNT KVDKTVERKC<br>CVECPPCPAP PVAGPSVFLF<br>PPKPKDTLMI SRTPEVTCVV<br>VDVSHEDPEV QFNWYVDGVE<br>VHNAKTKPRE EQFNSTFRVV<br>SVLTVVHQDW LNGKEYKCKV<br>SNKGLPAPIE KTISKTKGQP<br>REPQVYTLPP SREEMTKNQV<br>SLTCLVKGFY PSDIAVEWES<br>NGQPENNYKT TPPMLDSDGS<br>FFLYSKLTVD KSRWQQGNVF<br>SCSVMHEALH NHYTQKSLSL<br>SPG |
| SEQ ID NO: 8 | Heavy Chain, Variable Domain | EVQLLESGGG LVQPGGSLRL<br>SCAASGFTFS SYWMHWVRQA<br>PGKGLEWVSD IARLSSYTNY<br>ADSVKGRFTI SRDNSKNTLY<br>LQMNSLRAED TAVYYCARGL<br>DARRMDYWGQ GTLVTVSS |
| SEQ ID NO: 9 | Heavy Chain, Variable Domain, CDR1 | FSSYWMHW |
| SEQ ID NO: 10 | Heavy Chain, Variable Domain, CDR2 | SDIARLSSYT NYADSVKGR |

TABLE 1-continued

Heavy and Light Chain Sequences of Exemplary Human Anti-PRLR IgG2 Monoclonal Antibody Mat3-hIgG2

| Sequence Identifier | Portion of Antibody Chain | Amino Acid Sequence ($NH_3$—COOH) |
|---|---|---|
| SEQ ID NO: 11 | Heavy Chain, Variable Domain, CDR3 | ARGLDARRMD Y |
| SEQ ID NO: 12 | Heavy Chain, Constant Domain | ASTKGPSVFP LAPCSRSTSE STAALGCLVK DYFPEPVTVS WNSGALTSGV HTFPAVLQSS GLYSLSSVVT VPSSNFGTQT YTCNVDHKPS NTKVDKTVER KCCVECPPCP APPVAGPSVF LFPPKPKDTL MISRTPEVTC VVVDVSHEDP EVQFNWYVDG VEVHNAKTKP REEQFNSTFR VVSVLTVVHQ DWLNGKEYKC KVSNKGLPAP IEKTISKTKG QPREPQVYTL PPSREEMTKN QVSLTCLVKG FYPSDIAVEW ESNGQPENNY KTTPPMLDSD GSFFLYSKLT VDKSRWQQGN VFSCSVMHEA LHNHYTQKSL SLSPG |

Thus, the present disclosure provides anti-PRLR mAb formulations, including anti-PRLR IgG2 mAb formulations, wherein the anti-PRLR mAb is soluble at high protein concentrations. Typically, the anti-PRLR mAb in the formulations disclosed herein remain soluble at concentrations from about 1 mg/ml to about 150 mg/ml and remain stable under isosmotic storage conditions and exhibit reduced viscosity as compared to currently available antibody formulations.

The anti-PRLR antibody having a light chain sequence and a heavy chain sequence presented in one or more of PCT Patent Publication NOs. WO/2011/069799, WO/2011/069798, WO/2011/069797, WO/2011/069796, WO/2011/069795, and WO/2011/069794 can be an IgG2 antibody that blocks a prolactin receptor activity. Anti-PRLR antibodies can prevent the onset or progression of endometriosis by blocking PRLR, thereby overcoming deficiencies in endometrial pathways. The wide protein concentration range, including high concentration anti-PRLR antibody formulations presented herein can be administrated to the patients via intravenous injection intramuscular injection or subcutaneous injection.

The present disclosure also provides methods for the non-hormonal treatment of endometriosis in a patient, comprising the administration to the patient of a therapeutically effective amount of one or more formulations described herein. For example, provided are methods for the non-hormonal treatment of endometriosis in a patient, comprising the administration to the patient of a therapeutically effective amount of an anti-prolactin receptor antibody (aPRLR Ab) formulation including an aPRLR-specific IgG2 monoclonal antibody (mAb) formulation that contains from about 0 mM to about 30 mM phosphate; from about 50 ppm to about 200 ppm polysorbate (Tween®) 80 and/or polysorbate (Tween®) 20; from about 34 mM to about 292 mM sucrose; from about 0 mM to about 50 mM arginine, from about 0 mM to about 50 mM lysine, from about 0 mM to about 133 mM glycine or alanine, from about 0 mM to about 10 mM methionine, and from about 1 mg/ml to about 150 mg/ml of an anti-PRLR antibody at a pH ranging from about pH 5.5 to about pH6.5. Within at least one aspect of these methods, the anti-PRLR antibody formulation can be administered intravenously. Within other aspects of these methods, the anti-PRLR antibody formulation can be administered subcutaneously. Within other aspects of these methods, the anti-PRLR antibody formulation can be administered intramuscularly.

According to certain aspects of these methods for the non-hormonal treatment of endometriosis in a patient, the anti-PRLR antibody is a human anti-PRLR IgG2 monoclonal antibody such as, for example, a human anti-PRLR IgG2 monoclonal antibody that contains a light chain sequence and a heavy chain sequence presented in one or more of PCT Patent Publication NOs. WO/2011/069799, WO/2011/069798, WO/2011/069797, WO/2011/069796, WO/2011/069795, and WO/2011/069794.

Aspects of the present disclosure may be further understood in light of the following examples, which should not be construed as limiting the scope of the present teachings in any way.

EXAMPLES

Example 1

Effect of NaCl Concentration and pH on the Turbidity of Antibody Solutions

This Example discloses the effect of salt (NaCl) concentration and pH on the turbidity of solutions containing an anti-PRLR human monoclonal antibody that contains a light chain sequence and a heavy chain sequence presented in one or more of PCT Patent Publication Nos. WO/2011/069799, WO/2011/069798, WO/2011/069797, WO/2011/069796, WO/2011/069795, and WO/2011/069794. The turbidity of solutions is assessed by visual observation to quickly evaluate the effects of salt concentrations and pH on aPRLR mAb solutions. No precipitation is observed after 2 months at 5° C. and 25° C. with the formulation in absence of salt at pH 5.5-6.5.

Without being bound by theory, it is believed that the decreased stability in terms of turbidity or aggregation of the anti-PRLR mAb formulations with high NaCl concentration results from the neutralization of positive charges on the anti-PRLR mAb arginine side-chains. The phase behavior of aPRLR mAb at different pH with the impact of monovalent salt (NaCl) explains why the stable, soluble, non-salt, and substantial isosmolality aPRLR mAb formulations are achieved.

At a pH below the PI, such as pH 5.5-6.5, an anti-PRLR antibody has a net positive charge. The repulsion of the positive charges on such an anti-PRLR antibody surface likely prevents protein-protein association between individual molecules and, thereby, significantly increases solubility. It is hypothesized that the anion ($Cl^-$) of salt binds to the guanidinium group on arginine side-chains on an anti-PRLR antibody surface to neutralize the positive charges, which enhances protein-protein interactions and, hence, causes lower solubility and solution turbidity. By shifting the pH to 5.5-6.5, the non-salt formulations that are described herein are developed to achieve increased antibody solubility and stability. In absence of salt, the concentration of other stabilizers, such as sucrose, can be increased to >150 mM and <300 mM without compromising osmolality.

Example 2

Anti-PRLR Antibody Formulations

Substantially isosmotic high concentration anti-PRLR Ab formulations are prepared without NaCl. These formulations employ high sucrose concentrations to help stabilize the anti-PRLR Ab.

Frozen anti-PRLR antibody is thawed and reformulated by dialysis according to formulations presented in Table 2. The formulations are prepared and are sterile filtered with a 0.22 μm filter and sterile filled in glass tubing vials and stoppered with rubber stoppers.

In the absence of NaCl, and in the presence of sucrose or trehalose 88 mM to 292 mM and polysorbate 80 (50-200 ppm), the positive charged amino acids, such as arginine (10-50 mM), can effectively inhibit aPRLR Ab from degradation.

TABLE 2

Anti-PRLR Antibody Formulations 60 mg/mL aPRLR Ab
10 mM sodium phosphate
263 mM sucrose
80 ppm polysorbate 80
20 mM arginine
pH 6.5
60 mg/mL aPRLR Ab
10 mM sodium phosphate
263 mM sucrose
80 ppm polysorbate 80
20 mM arginine
pH 6.0
60 mg/mL aPRLR Ab
10 mM sodium phosphate
263 mM sucrose
80 ppm polysorbate 80
pH 5.5
60 mg/mL aPRLR Ab
10 mM sodium phosphate
263 mM sucrose
80 ppm polysorbate 80
10 mM arginine
1 mM methionine
pH 6.0
60 mg/mL aPRLR Ab TABLE 2-continued Anti-PRLR Antibody Formulations 10 mM sodium phosphate
263 mM sucrose
80 ppm polysorbate 80
arginine 10 mM
methionine 1 mM
pH 6.5

Representative anti-PRLR mAb formulations were analyzed by HPLC-SEC for protein aggregation and degradation, LC-MS for aPRLR structural changes (glycation and oxidation), nephlometry for turbidity assessment, viscometer for viscosity measurement, and osmolality instrument for osmolality measurement. The results for the HPLC-SEC analysis of protein aggregation are presented in Tables 3A and 3B, the results for the nephlometry analysis of turbidity are presented in Table 4, the results for the LC-MS analysis of aPRLR structural changes are presented in Table 5, and the results for the analysis of viscosity and osmolality are presented in Table 6.

TABLE 3A

HPLC-SEC Average Rate of Aggregation Formation (%/day)

| Formulation Composition | | 5° C. | 25° C. |
|---|---|---|---|
| Anti-PRLR | 60 mg/mL | 0.014[1] | 0.029[1] |
| Sodium phosphate | 10 mM | | |
| Sucrose | 263 mM | | |
| Polysorbate 80 | 80 ppm | | |
| pH | 6.5 | | |
| Arginine | 20 mM | | |
| Anti-PRLR | 60 mg/mL | 0.012[1] | 0.023[1] |
| Sodium phosphate | 10 mM | | |
| Sucrose | 263 mM | | |
| Polysorbate 80 | 80 ppm | | |
| pH | 6.0 | | |
| Arginine | 20 mM | | |
| Anti-PRLR | 60 mg/mL | 0.014[1] | 0.022[1] |
| Sodium phosphate | 10 mM | | |
| Sucrose | 263 mM | | |
| Polysorbate 80 | 80 ppm | | |
| pH | 5.5 | | |

TABLE 3B

HPLC-SEC Average Rate of Aggregation Formation (%/day)

| Formulation Composition | | 5° C. | 25° C. |
|---|---|---|---|
| Anti-PRLR | 60 mg/mL | 0.004[1] | 0.011[1] |
| Sodium phosphate | 10 mM | | |
| Sucrose | 263 mM | | |
| Polysorbate 80 | 80 ppm | | |
| pH | 6.5 | | |
| Arginine | 20 mM | | |
| Anti-PRLR | 60 mg/mL | 0.004[1] | 0.008[1] |
| Sodium phosphate | 10 mM | | |
| Sucrose | 263 mM | | |
| Polysorbate 80 | 80 ppm | | |
| pH | 6.0 | | |
| Arginine | 20 mM | | |
| Anti-PRLR | 60 mg/mL | 0.004[1] | 0.007[1] |
| Sodium phosphate | 10 mM | | |
| Sucrose | 263 mM | | |
| Polysorbate 80 | 80 ppm | | |
| pH | 5.5 | | |

[1]The calculation values were based on 90 days as shown in Table 3A and 12 months as shown in Table 3B.

TABLE 4

LC-MS Results of the Formulations after Shaking at 100 rpm at Room Temperature

| Formulation Composition | | Intact Mass | Mass of LC and HC |
|---|---|---|---|
| Anti-PRLR | 60 mg/mL | Comparable to RS [1] | Comparable to RS [1] |
| Sodium phosphate | 10 mM | | |
| Sucrose | 263 mM | | |
| Polysorbate 80 | 80 ppm | | |
| pH | 6.5 | | |
| Arginine | 20 mM | | |
| Anti-PRLR | 60 mg/mL | Comparable to RS [1] | Comparable to RS [1] |
| Sodium phosphate | 10 mM | | |
| Sucrose | 263 mM | | |
| Polysorbate 80 | 80 ppm | | |
| pH | 6.0 | | |
| Arginine | 20 mM | | |
| Anti-PRLR | 60 mg/mL | Comparable to RS [1] | Comparable to RS [1] |
| Sodium phosphate | 10 mM | | |
| Sucrose | 263 mM | | |
| Polysorbate 80 | 80 ppm | | |
| pH | 5.5 | | |

[1] After the formulation was shaken at 100 rpm at room temperature for 21 days.
LC = Light Chain; HC = Heavy Chain; RS = Reference Standard.

TABLE 5

Average Rate of Turbidity change (by Nephelometry) after Shaking at 100 rpm at Room Temperature

| Formulation Composition | | FNU/day |
|---|---|---|
| Anti-PRLR | 60 mg/mL | 0.029[1] |
| Sodium phosphate | 10 mM | |
| Sucrose | 263 mM | |
| Polysorbate 80 | 80 ppm | |
| pH | 6.5 | |
| Arginine | 20 mM | |
| Anti-PRLR | 60 mg/mL | 0.018[1] |
| Sodium phosphate | 10 mM | |
| Sucrose | 263 mM | |
| Polysorbate 80 | 80 ppm | |
| pH | 6.0 | |
| Arginine | 20 mM | |
| Anti-PRLR | 60 mg/mL | 0.003[1] |
| Sodium phosphate | 10 mM | |
| Sucrose | 263 mM | |
| Polysorbate 80 | 80 ppm | |
| pH | 5.5 | |

[1] After the formulation was shaken at 100 rpm at room temperature for 21 days.

TABLE 6

Viscosity and Osmolality of Anti-PRLR Ab Formulations

| Formulation Composition | | Viscosity (mPa-S) at 22-23° C. | Osmolality (mmol/kg) |
|---|---|---|---|
| Anti-PRLR | 60 mg/mL | 2.49 | 357 |
| Sodium phosphate | 10 mM | | |
| Sucrose | 263 mM | | |
| Polysorbate 80 | 80 ppm | | |
| pH | 6.5 | | |
| Arginine | 20 mM | | |
| Anti-PRLR | 60 mg/mL | 2.41 | 360 |
| Sodium phosphate | 10 mM | | |
| Sucrose | 263 mM | | |
| Polysorbate 80 | 80 ppm | | |
| pH | 6.0 | | |
| Arginine | 20 mM | | |
| Anti-PRLR | 60 mg/mL | 2.30 | 313 |
| Sodium phosphate | 10 mM | | |
| Sucrose | 263 mM | | |
| Polysorbate 80 | 80 ppm | | |
| pH | 5.5 | | |
| Anti-PRLR | 60 mg/mL | 1.88 | 348 |
| Sodium phosphate | 10 mM | | |
| Sucrose | 263 mM | | |
| Polysorbate 80 | 80 ppm | | |
| pH | 6.0 | | |
| Arginine | 10 mM | | |
| Methionine | 1 mM | | |
| Anti-PRLR | 60 mg/mL | 1.91 | 343 |
| Sodium phosphate | 10 mM | | |
| Sucrose | 263 mM | | |
| Polysorbate 80 | 80 ppm | | |
| pH | 6.5 | | |
| Arginine | 10 mM | | |
| Methionine | 1 mM | | |

What is claimed is:

1. An anti-PRLR antibody formulation, comprising:
   a. 10 mM to 30 mM phosphate;
   b. 50 ppm to 200 ppm of a non-ionic surfactant;
   c. 34 mM to 292 mM of a sugar selected from mannitol, dextrose, glucose, trehalose, and sucrose;
   d. 0 mM to 50 mM arginine;
   e. 0 mM to 50 mM lysine;
   f. 0 mM to 270 mM glycine or alanine;
   g. 0 mM to 10 mM methionine; and
   h. 0.1 mg/ml to 150 mg/ml of an anti-PRLR antibody;
   wherein said anti-PRLR antibody formulation has a pH ranging from pH 5.5 to pH 6.5.

2. The anti-PRLR antibody formulation of claim 1 wherein said formulation has a viscosity ranging from about 1 mPa-S to about 8 mPa-S at 22° C.-23° C.

3. The anti-PRLR antibody formulation of claim 1 wherein said formulation has and osmolality ranging from about 240 mmol/kg to about 380 mmol/kg.

4. The anti-PRLR antibody formulation of any of claim 1 wherein said non-ionic surfactant is a polysorbate selected from polysorbate 20 and polysorbate 80.

5. The anti-PRLR antibody formulation of claim 1 wherein said sugar is sucrose or trehalose.

6. The anti-PRLR antibody formulation of claim 1 comprising from about 10 mM to about 50 mM arginine.

7. The anti-PRLR antibody formulation of claim 1, comprising from about 5 mM to about 10 mM methionine.

8. The anti-PRLR antibody formulation of claim 1, comprising:
   a. 10 mM sodium phosphate,
   b. 263 mM sucrose,
   c. 80 ppm polysorbate 80,
   d. 20 mM arginine,
   e. 60 mg/mL anti-PRLR antibody;
   wherein said anti-PRLR antibody formulation has a pH of 6.5.

9. The anti-PRLR antibody formulation of claim 1, comprising:
   a. 10 mM sodium phosphate,
   b. 263 mM sucrose,
   c. 80 ppm polysorbate 80,
   d. 20 mM arginine,
   e. 60 mg/mL anti-PRLR antibody;
   wherein said anti-PRLR antibody formulation has a pH of 6.0.

10. The anti-PRLR antibody formulation of claim 1, comprising:
    a. 10 mM sodium phosphate,
    b. 263 mM sucrose,
    c. 80 ppm polysorbate 80,
    d. 60 mg/mL anti-PRLR antibody;
    wherein said anti-PRLR antibody formulation has a pH of 5.5.

11. The anti-PRLR antibody formulation of claim 1, comprising:
    a. 10 mM sodium phosphate,
    b. 263 mM sucrose,
    c. 80 ppm polysorbate 80,
    d. 10 mM arginine,
    e. 10 mM methionine,
    f. 60 mg/mL anti-PRLR antibody;
    wherein said anti-PRLR antibody formulation has a pH of 6.0.

12. The anti-PRLR antibody formulation of claim 1, comprising:
    a. 10 mM sodium phosphate,
    b. 263 mM sucrose,
    c. 80 ppm polysorbate 80,
    d. 10 mM arginine,
    e. 5 mM methionine,
    f. 60 mg/mL anti-PRLR antibody;
    wherein said anti-PRLR antibody formulation has a pH of 6.5.

13. The anti-PRLR antibody formulation of claim 1 wherein said anti-PRLR antibody is a human IgG2 monoclonal antibody.

14. The anti-PRLR antibody formulation of claim 13 wherein said human IgG2 monoclonal antibody comprises a light chain sequence of SEQ ID NO: 1 and a heavy chain sequence of SEQ ID NO: 7.

15. A method for the non-hormonal treatment of endometriosis in a patient, said method comprising administering to said patient a therapeutically effective amount of a neutralizing anti-PRLR antibody formulation comprising between 10 mM and 30 mM phosphate, between 50 ppm and 200 ppm polysorbate 80 or polysorbate 20, between 34 mM and 292 mM sucrose or trehalose, between 0 mM and 50 mM arginine, between 0 mM and 50 mM lysine, between 0 mM and 270 mM glycine or alanine, between 0 mM and 10 mM methionine, and between 0.1 mg/ml and 150 mg/ml of a protein or antibody at a pH of between pH 5.5 and pH 6.5.

16. The method of claim 15 wherein said anti-PRLR antibody formulation is administered intravenously, subcutaneously, or intramuscularly.

17. The method of claim 15 wherein said anti-PRLR antibody is a human IgG2 monoclonal antibody.

18. The method of claim 17 wherein said human IgG2 monoclonal antibody comprises a light chain sequence of SEQ ID NO: 1 and a heavy chain sequence of SEQ ID NO: 7.

* * * * *

```
SEQUENCE LISTING

<160> NUMBER OF SEQ ID NOS: 12

<210> SEQ ID NO 1
<211> LENGTH: 217
<212> TYPE: PRT
<213> ORGANISM: Artificial Sequence
<220> FEATURE:
<223> OTHER INFORMATION: Anti-PRLR IgG2 Monoclonal Antibody Mat3-hIgG2,
      Light Chain, Full-length

<400> SEQUENCE: 1

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Val Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
```

```
                50                  55                  60
Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Trp Leu Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
            195                 200                 205

Lys Thr Val Ala Pro Thr Glu Cys Ser
            210                 215
```

```
<210> SEQ ID NO 2
<211> LENGTH: 217
<212> TYPE: PRT
<213> ORGANISM: Artificial Sequence
<220> FEATURE:
<223> OTHER INFORMATION: Anti-PRLR IgG2, Monoclonal Antibody Mat3-hIgG2,
      Light Chain, Variable Domain

<400> SEQUENCE: 2

Gln Ser Val Leu Thr Gln Pro Pro Ser Ala Ser Gly Thr Pro Gly Gln
  1               5                  10                  15

Arg Val Thr Ile Ser Cys Thr Gly Ser Ser Ser Asn Ile Gly Ala Gly
                 20                  25                  30

Tyr Val Val His Trp Tyr Gln Gln Leu Pro Gly Thr Ala Pro Lys Leu
             35                  40                  45

Leu Ile Tyr Arg Asn Asn Gln Arg Pro Ser Gly Val Pro Asp Arg Phe
 50                  55                  60

Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Trp Leu Phe Gly Gly Gly Thr Lys Leu Thr Val Leu Gly
                100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190
```

```
His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 3
<211> LENGTH: 16
<212> TYPE: PRT
<213> ORGANISM: Artificial Sequence
<220> FEATURE:
<223> OTHER INFORMATION: Anti-PRLR IgG2, Monoclonal Antibody Mat3-hIgG2,
      Light Chain, Variable Domain, CDR1

<400> SEQUENCE: 3

Ser Cys Thr Gly Ser Ser Ser Asn Ile Gly Ala Gly Tyr Val Val His
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Anti-PRLR IgG2, Monoclonal Antibody Mat3-hIgG2,
      Light Chain, Variable Domain, CDR2

<400> SEQUENCE: 4

Arg Asn Asn Gln Arg Pro Ser
1               5

<210> SEQ ID NO 5
<211> LENGTH: 12
<212> TYPE: PRT
<213> ORGANISM: Artificial Sequence
<220> FEATURE:
<223> OTHER INFORMATION: Anti-PRLR IgG2, Monoclonal Antibody Mat3-hIgG2,
      Light Chain, Variable Domain, CDR3

<400> SEQUENCE: 5

Cys Ala Ala Trp Asp Asp Ser Leu Asn Gly Trp Leu
1               5                   10

<210> SEQ ID NO 6
<211> LENGTH: 104
<212> TYPE: PRT
<213> ORGANISM: Artificial Sequence
<220> FEATURE:
<223> OTHER INFORMATION: Anti-PRLR IgG2, Monoclonal Antibody Mat3-hIgG2,
      Light Chain, Constant Domain

<400> SEQUENCE: 6

Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100
```

<210> SEQ ID NO 7
<211> LENGTH: 443
<212> TYPE: PRT
<213> ORGANISM: Artificial Sequence
<220> FEATURE:
<223> OTHER INFORMATION: Anti-PRLR IgG2, Monoclonal Antibody Mat3-hIgG2, Heavy Chain, Full-length

<400> SEQUENCE: 7

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Asp Ile Ala Arg Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Met Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
```

```
                    355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 8
<211> LENGTH: 118
<212> TYPE: PRT
<213> ORGANISM: Artificial Sequence
<220> FEATURE:
<223> OTHER INFORMATION: Anti-PRLR IgG2, Monoclonal Antibody Mat3-hIgG2,
      Heavy Chain, Variable Domain

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Glu Trp Val
        35                  40                  45

Ser Asp Ile Ala Arg Leu Ser Ser Tyr Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Ala Arg Arg Met Asp Tyr Trp Gly Gln Gly Thr
            100                 105                 110

Leu Val Thr Val Ser Ser
        115

<210> SEQ ID NO 9
<211> LENGTH: 8
<212> TYPE: PRT
<213> ORGANISM: Artificial Sequence
<220> FEATURE:
<223> OTHER INFORMATION: Anti-PRLR IgG2, Monoclonal Antibody Mat3-hIgG2,
      Heavy Chain, Variable Domain, CDR1

<400> SEQUENCE: 9

Phe Ser Ser Tyr Trp Met His Trp
1               5

<210> SEQ ID NO 10
<211> LENGTH: 19
<212> TYPE: PRT
<213> ORGANISM: Artificial Sequence
<220> FEATURE:
<223> OTHER INFORMATION: Anti-PRLR IgG2, Monoclonal Antibody Mat3-hIgG2,
      Heavy Chain, Variable Domain, CDR2

<400> SEQUENCE: 10

Ser Asp Ile Ala Arg Leu Ser Ser Tyr Thr Asn Tyr Ala Asp Ser Val
1               5                   10                  15
```

Lys Gly Arg

<210> SEQ ID NO 11
<211> LENGTH: 11
<212> TYPE: PRT
<213> ORGANISM: Artificial Sequence
<220> FEATURE:
<223> OTHER INFORMATION: Anti-PRLR IgG2, Monoclonal Antibody Mat3-hIgG2,
      Heavy Chain, Variable Domain, CDR3

<400> SEQUENCE: 11

Ala Arg Gly Leu Asp Ala Arg Arg Met Asp Tyr
1               5                   10

<210> SEQ ID NO 12
<211> LENGTH: 325
<212> TYPE: PRT
<213> ORGANISM: Artificial Sequence
<220> FEATURE:
<223> OTHER INFORMATION: Anti-PRLR IgG2, Monoclonal Antibody Mat3-hIgG2,
      Heavy Chain, Constant Domain

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

-continued

```
Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325
```